(12) United States Patent
Chen

(10) Patent No.: US 12,408,977 B2
(45) Date of Patent: Sep. 9, 2025

(54) METHODS FOR MONITORING ABLATION PROGRESS WITH DOPPLER ULTRASOUND

(71) Applicant: Gynesonics, Inc., Redwood City, CA (US)

(72) Inventor: Jiayu Chen, Palo Alto, CA (US)

(73) Assignee: Gynesonics, Inc., Redwood City, CA (US)

( * ) Notice: Subject to any disclaimer, the term of this patent is extended or adjusted under 35 U.S.C. 154(b) by 0 days.

(21) Appl. No.: 18/173,000

(22) Filed: Feb. 22, 2023

(65) Prior Publication Data
US 2024/0024023 A1 Jan. 25, 2024

Related U.S. Application Data

(63) Continuation of application No. 16/666,271, filed on Oct. 28, 2019, now Pat. No. 11,612,431, which is a
(Continued)

(51) Int. Cl.
*A61B 18/14* (2006.01)
*A61B 90/00* (2016.01)
*A61B 18/00* (2006.01)

(52) U.S. Cl.
CPC ...... *A61B 18/1492* (2013.01); *A61B 18/1477* (2013.01); *A61B 90/37* (2016.02);
(Continued)

(58) Field of Classification Search
CPC ............ A61B 18/1477; A61B 18/1492; A61B 2017/00128; A61B 2018/00577;
(Continued)

(56) References Cited

U.S. PATENT DOCUMENTS 5,979,453 A * 11/1999 Savage .................. A61N 1/403
606/41
6,315,730 B1 * 11/2001 Hoff ....................... A61B 8/481
600/458
(Continued)

FOREIGN PATENT DOCUMENTS

| CN | 102238921 A | 11/2011 |
| JP | 2007244857 A | 9/2007 |

(Continued)

OTHER PUBLICATIONS

EP18794337.8 Extended European Search Report dated Feb. 8, 2021.
(Continued)

*Primary Examiner* — Michael F Peffley
(74) *Attorney, Agent, or Firm* — Vista IP Law Group, LLP

(57) ABSTRACT

Systems and methods for treating tissue are disclosed. The target tissue is ablated. A real-time image of the target tissue is generated during the ablation. The real-time blood perfusion level of the target tissue is determined from the real-time image and compared to an initial blood perfusion level of the target tissue. The comparison provides a metric for the progress of the ablation, and ablation is halted when the real-time blood perfusion drops below a threshold level relative to the initial blood perfusion level.

20 Claims, 15 Drawing Sheets

Related U.S. Application Data continuation of application No. PCT/US2018/030295, filed on Apr. 30, 2018.

(60) Provisional application No. 62/501,238, filed on May 4, 2017.

(52) U.S. Cl.
CPC .............. *A61B 2018/00577* (2013.01); *A61B 2018/143* (2013.01); *A61B 2090/378* (2016.02)

(58) Field of Classification Search
CPC ........... A61B 2018/00863; A61B 2018/00982; A61B 2018/143; A61B 2018/1475; A61B 8/06; A61B 8/481; A61B 8/488; A61B 90/37

See application file for complete search history.

(56) References Cited

U.S. PATENT DOCUMENTS

| | | |
|---|---|---|
| 6,540,677 B1 | 4/2003 | Angelsen et al. |
| 6,575,969 B1* | 6/2003 | Rittman, III ....... A61B 18/1482 606/41 |
| 6,602,251 B2 | 8/2003 | Burbank et al. |
| 6,623,481 B1 | 9/2003 | Garbagnati et al. |
| 6,936,048 B2 | 8/2005 | Hurst |
| 6,944,490 B1 | 9/2005 | Chow |
| 6,969,354 B1 | 11/2005 | Marian |
| 7,160,296 B2 | 1/2007 | Pearson et al. |
| 7,229,401 B2 | 6/2007 | Kindlein |
| 7,387,628 B1 | 6/2008 | Behl et al. |
| 7,517,346 B2 | 4/2009 | Sloan et al. |
| 7,918,795 B2 | 4/2011 | Grossman |
| 7,963,941 B2 | 6/2011 | Wilk |
| 8,080,009 B2 | 12/2011 | Lee et al. |
| 8,157,741 B2 | 4/2012 | Hirota |
| 8,157,745 B2 | 4/2012 | Schoot |
| 8,206,300 B2 | 6/2012 | Deckman et al. |
| 8,216,231 B2 | 7/2012 | Behl et al. |
| 8,221,321 B2 | 7/2012 | McMorrow et al. |
| 8,262,574 B2 | 9/2012 | Placek et al. |
| 8,287,485 B2 | 10/2012 | Kimura et al. |
| 8,377,041 B2 | 2/2013 | Frassica et al. |
| 8,469,893 B2 | 6/2013 | Chiang et al. |
| 8,506,485 B2 | 8/2013 | Deckman et al. |
| 8,512,330 B2 | 8/2013 | Epstein et al. |
| 8,512,333 B2 | 8/2013 | Epstein et al. |
| 8,540,634 B2 | 9/2013 | Bruce et al. |
| 8,585,598 B2 | 11/2013 | Razzaque et al. |
| 8,622,911 B2 | 1/2014 | Hossack et al. |
| 8,663,130 B2 | 3/2014 | Neubach et al. |
| 8,718,339 B2 | 5/2014 | Tonomura et al. |
| 8,814,796 B2 | 8/2014 | Martin et al. |
| 8,992,427 B2 | 3/2015 | Munrow et al. |
| 9,089,287 B2 | 7/2015 | Sliwa et al. |
| 9,119,649 B2 | 9/2015 | Van et al. |
| 9,198,707 B2 | 12/2015 | McKay et al. |
| 9,198,719 B2 | 12/2015 | Murdeshwar et al. |
| 9,247,925 B2 | 2/2016 | Havel et al. |
| 9,439,627 B2 | 9/2016 | Case et al. |
| 9,510,898 B2 | 12/2016 | Epstein et al. |
| 9,516,996 B2 | 12/2016 | Diolaiti et al. |
| 9,517,047 B2 | 12/2016 | Grossman |
| 10,595,819 B2* | 3/2020 | Deckman ............. A61B 8/4461 |
| 11,612,431 B2 | 3/2023 | Chen |
| 2001/0014805 A1 | 8/2001 | Burbank et al. |
| 2007/0208327 A1 | 9/2007 | Rosemberg et al. |
| 2008/0228081 A1 | 9/2008 | Becker et al. |
| 2009/0043295 A1 | 2/2009 | Arnal et al. |
| 2009/0093718 A1 | 4/2009 | Jibiki et al. |
| 2010/0160781 A1 | 6/2010 | Carter et al. |
| 2010/0262133 A1 | 10/2010 | Hoey et al. |
| 2010/0312117 A1* | 12/2010 | Fernandez ............. A61B 8/463 600/458 |
| 2011/0098564 A1 | 4/2011 | Larson et al. |
| 2011/0208061 A1 | 8/2011 | Chang |
| 2012/0010479 A1 | 1/2012 | Eusemann et al. |
| 2012/0035474 A1 | 2/2012 | Deckman et al. |
| 2012/0165813 A1 | 6/2012 | Lee et al. |
| 2012/0209115 A1 | 8/2012 | Tonomura |
| 2012/0277737 A1 | 11/2012 | Curley |
| 2012/0316440 A1 | 12/2012 | Munrow et al. |
| 2013/0041259 A1 | 2/2013 | Harks et al. |
| 2013/0085497 A1* | 4/2013 | Chang ................... A61B 17/32 606/45 |
| 2013/0281863 A1 | 10/2013 | Chiang et al. |
| 2013/0317366 A1 | 11/2013 | Hirayama et al. |
| 2014/0073911 A1 | 3/2014 | Munrow et al. |
| 2014/0180273 A1 | 6/2014 | Nair |
| 2014/0276081 A1 | 9/2014 | Tegels |
| 2015/0150497 A1 | 6/2015 | Goldchmit |
| 2015/0173592 A1 | 6/2015 | Leeflang et al. |
| 2015/0257779 A1 | 9/2015 | Sinelnikov et al. |
| 2015/0335344 A1* | 11/2015 | Aljuri ................ A61B 18/1485 606/169 |
| 2016/0051221 A1 | 2/2016 | Dickhans et al. |
| 2016/0151041 A1 | 6/2016 | Lee et al. |
| 2016/0249878 A1 | 9/2016 | Grossman |
| 2016/0278740 A1 | 9/2016 | Negrila et al. |
| 2016/0310042 A1 | 10/2016 | Kesten et al. |

FOREIGN PATENT DOCUMENTS

| | | |
|---|---|---|
| JP | 2009136523 A | 6/2009 |
| JP | 2013500778 A | 1/2013 |
| JP | 2013527782 A | 7/2013 |
| JP | 2013529943 A | 7/2013 |
| WO | WO-2009027890 A1 | 3/2009 |
| WO | WO-2015087203 A1 | 6/2015 |
| WO | WO-2018201158 A1 | 11/2018 |
| WO | WO-2018204284 A1 | 11/2018 |

OTHER PUBLICATIONS

International Search Report and Written Opinion for PCT/US2018/30295 on Sep. 13, 2018.

U.S. Appl. No. 16/666,271 Notice of Allowance dated Nov. 30, 2022.

U.S. Appl. No. 16/666,271 Office Action dated Dec. 10, 2021.

U.S. Appl. No. 16/666,271 Office Action dated Jul. 1, 2022.

\* cited by examiner

METHODS FOR MONITORING ABLATION PROGRESS WITH DOPPLER ULTRASOUND

CROSS-REFERENCE

This application is a continuation of U.S. patent application Ser. No. 16/666,271, filed Oct. 28, 2019, now U.S. Pat. No. 11,612,431; which is a continuation of PCT Application No. PCT/US18/30295, filed Apr. 30, 2018; which claims the benefit of U.S. Provisional Application No. 62/501,238, filed May 4, 2017; all of which are incorporated in their entirety herein by reference.

BACKGROUND OF THE INVENTION

1. Field of the Invention

The present invention relates generally to medical methods and apparatus. More particularly, the present invention relates to methods and systems for displaying in real-time an image of tissue to be treated such that the treatment can be controlled.

Current medical treatments of organs and tissues within a patient's body often use a needle or other elongate body for delivery of energy, therapeutic agents, or the like. Often, the methods use ultrasound imaging to observe and identify a treatment target before, during, and/or after.

Of particular interest to the present invention, a treatment for uterine fibroids has recently been proposed which relies on the transvaginal or laparoscopic positioning of a treatment probe or device in the patient's uterus. A radiofrequency or other energy or therapeutic delivery needle is deployed from the device in proximity to or directly into the fibroid, and energy and/or therapeutic substances are delivered in order to ablate or treat the fibroid. To facilitate locating the fibroids and positioning the needles within the fibroids, the treatment device includes an ultrasonic imaging array with an adjustable field of view in a generally forward or lateral direction relative to an axial shaft which carries the needle. The needle is advanced from the shaft and across the field of view so that the needle can be visualized and directed into the tissue and the targeted fibroid.

While effective and very beneficial for patients, such needle ablation and treatment protocols face several challenges. While the position of the needle can be observed on the ultrasonic or other visual image, the treatment volume resulting from energy or other therapeutic delivery can be difficult to predict. One of reasons may be that the energy propagation within the tissue may largely depend on the tissue structure and the distribution of blood vessels which can act as "heatsinks." The coagulation sizes introduced by RF ablation may vary from tumor to tumor because of the distribution of the blood vessels. Current coagulation size and safety margin are typically based on a static size prediction which could affect the efficacy and even safety of the treatment. The experience of the physician can help to determine an appropriate end point for the ablation, but it would be desirable to reduce the need to exercise judgment and conjecture.

Tissue heating or cooling may be affected by adjacent vasculature, as blood vessels can dissipate thermal energy and cause variation on the calculated coagulation size. Thus, thermal ablation size and cytotoxic effectiveness may decrease with the proximity and the size of adjacent vessels. Increased local recurrence rates of tumors adjacent to large vessels (>3 mm) can demonstrate the significant effect of thermal energy sinks. The distortion of the perivascular margin may be present approximately one-third of the ablations. The extent of the heat sink effect may significantly correlate with the size of the vessel. Multiple studies have also examined the effects of modulating hepatic perfusion and have found that the ablation size increases with decreased blood flow. Developing methods to better estimate or monitor the ablation size will be beneficial to both efficacy and safety of treatments.

For these reasons, it would be desirable to provide improved systems and methods for the deployment of energy delivery and other needles within ultrasonic or other imaging fields of view in energy delivery or other therapeutic protocols. It would be particularly useful to provide the treating physician with information which would assist determining the real-time progress of the ablation. It would also be desirable to provide feedback to the physician to assist in accurately predicting a treatment volume. Such information should allow the physician, if necessary, to end an ablation protocol at an appropriate time when the desired target tissue has been fully or near fully ablated while unintentional ablation of non-target tissue is reduced. Furthermore, it would be desirable to provide feedback to the physician allowing the physician to assess a safety margin so that sensitive tissue structures are not damaged. All such feedback or other information is preferably provided visually on the ultrasonic or other imaging screen so that the physician can start, pause, and stop the treatment. At least some of these objectives will be met by the inventions described hereinafter.

2. Description of the Background Art

Ultrasound (US) is the primary imaging modality used to evaluate patients in whom the presence of uterine fibroid tumors is suspected. Trans-abdominal and transvaginal US are used in conjunction with color and pulsed Doppler US. Doppler US can be used to assess fibroid and uterine vascularity and flow patterns. Typically, uterine fibroid tumors have a marked peripheral blood flow (perifibroid plexus) and decreased central flow. The resistance index is usually decreased in the perifibroid plexus, compared with that in the surrounding normal myometrium.

Contrast-enhanced ultrasound (CEUS) is a technique that makes use of microbubble-based contrast agents to improve the echogenicity of blood and thus improve the visualization and assessment of cardiac cavities, large vessels, and tissue vascularity. Ultrasound contrast agents offer high sensitivity with a safety profile. CEUS offers additional advantages over the alternative imaging modalities. It can be performed immediately after baseline ultrasound, the first-line imaging modality in many clinical settings, and it can be carried out in a variety of scenarios (clinical office setting, operating room, etc.). It does not involve exposure to ionizing radiations, and it allows prolonged real time examinations where also rapid changes can be captured, or the study repeated if needed.

References that may be of interest include: U.S. Pat. No. 5,979,453 to Savage et al., U.S. Pat. No. 6,602,251 to Burbank et al., U.S. Pat. No. 7,918,795 to Grossma , U.S. Pat. No. 8,506,485 to Deckman et al., U.S. Pat. No. 8,992,427 to Munrow et al., and U.S. Pat. No. 9,517,047 to Grossman.

SUMMARY OF THE INVENTION

The present disclosure provides systems and methods for treating tissue structures. In particular, systems and methods for ablating tissue structures and monitoring the ablation are provided. A real-time image of a target tissue structure, such as a uterine fibroid, may be displayed. The real-time image may also show the blood flow and/or perfusion within the target tissue structure. For example, the real-time image may comprise a Doppler ultrasound image and/or a contrast enhanced ultrasound imaging (CEUS) to show the blood perfusion. The image showing the blood perfusion may be overlaid with an image showing the morphology and/or density of the target tissue structure. As the target tissue is ablated, the blood perfusion of the target tissue may be reduced and/or the size of the reduced blood perfusion area may be increased. By displaying to the physician or user a real-time image of the target tissue showing the tissue morphology and blood perfusion during ablation, the physician or user can track the progress of the treatment. For instance, once the blood perfusion of the target is reduced by a threshold amount as compared to its initial blood perfusion level and/or once the size of the reduced blood perfusion area reaches a threshold size, the user may halt the ablation to ensure that the target tissue structure is fully or near fully ablated and the undesired ablation of non-targeted is minimized. Furthermore, the effectiveness and safety of the treatment may be ensured by displaying the real-time image of the target tissue, which can allow the movement of perfusion boundaries, the effective edge of ablation, to be monitored in real-time.

Aspects of the present disclosure provide exemplary methods of treating a target tissue. The target tissue may be ablated. A real-time image of the target tissue may be generated during the ablating. The image may show blood perfusion of the target tissue as the target tissue is ablated. The image showing blood perfusion of the target tissue may be displayed, thereby indicating to a user a progress of the ablation.

A real-time blood perfusion level of the target tissue may be determined, and it may be determined whether the real-time blood perfusion level is below a threshold amount. An initial blood perfusion level of the target tissue may be determined, and the threshold amount may be 50% or less, 45% or less, 40% or less, 35% or less, 30% or less, 25% or less, 20% or less, 15% or less, 10% or less, or 5% or less of the initial blood perfusion level of the target tissue. The user may be indicated or instructed to halt the ablating of the target tissue in response to the real-time blood perfusion level being below the threshold amount. Alternatively or in combination, the ablating of the target tissue may be halted, for example, automatically halted, in response to the real-time blood perfusion level being below the threshold amount. The initial blood perfusion level may comprise an initial Doppler ultrasound signal within the target tissue, and the real-time blood perfusion level may comprise a real-time Doppler ultrasound signal within the target tissue.

A position of an imaging source may be fixed in relation to the target tissue. The real-time image of the target tissue may be generated during the ablating with the position of the imaging source fixed in relation to the target tissue. The target tissue may be ablated with an ablation element. The imaging source may be fixedly coupled to the ablation element. Alternatively or in combination, the imaging source may be removably coupled to the ablation element.

The real-time image of the target tissue may be generated by generating at least one ultrasound image of the target tissue. The at least one ultrasound image may comprise one or more of a contrast enhanced ultrasound image, a B-mode ultrasound image, or a Doppler ultrasound image. The at least one ultrasound image may comprise a B-mode ultrasound image and a Doppler ultrasound image overlaid over one another. Common anatomical markers in the two images may be identified and mapped to one another to generate the overlaid image. In some cases, a contrast agent may be introduced into the target tissue prior to the ablation to provide more enhanced ultrasound images.

The target tissue may be ablated with one or more of RF energy, thermal energy, cryo energy, ultrasound energy, HIFU energy, optical energy, laser energy, X-ray energy, or microwave energy. The target tissue may be ablated by extending at least one ablation element into the target tissue. The at least one ablation element may comprise one or more of at least one needle or at least one tine. The target tissue may comprise a fibroid, a uterine fibroid, a fibroid tissue, a tumor, a tissue hyperplasia, or an undesired scar tissue.

Aspects of the present disclosure provide further methods of treating a target tissue. The target tissue may be ablated. The progress of the ablating of the target tissue may be monitored by viewing a real-time image of the target tissue to monitor blood perfusion of the target tissue.

To monitor the progress of the ablating of the target tissue by viewing the real-time image of the target tissue to monitor blood perfusion of the target tissue comprises, an initial blood perfusion level of the target tissue may be determined, a real-time blood perfusion level of the target tissue may be determined, and the initial and real-time blood perfusion levels of the target tissue may be compared. To compare the initial and real-time blood perfusion levels of the target tissue, it may be determined whether the real-time blood perfusion level of the target tissue is below the initial blood perfusion level by a threshold amount. The ablating of the target tissue may be halted once the blood perfusion of the target tissue is below the threshold amount. The threshold amount may be 50% or less, 45% or less, 40% or less, 35% or less, 30% or less, 25% or less, 20% or less, 15% or less, 10% or less, or 5% or less of an initial blood perfusion amount of the target tissue. The initial blood perfusion level may comprise an initial Doppler ultrasound signal within the target tissue. The real-time blood perfusion level may comprise a real-time Doppler ultrasound signal within the target tissue.

A position of an imaging source in relation to the target tissue may be fixed. The real-time image of the target tissue may be generated during the ablating with the position of the imaging source fixed in relation to the target tissue. The target tissue may be ablated with an ablation element. The imaging source may be fixedly coupled to the ablation element. Alternatively or in combination, the imaging source may be removably coupled to the ablation element.

The real-time image of the target tissue may comprise at least one ultrasound image of the target tissue. The at least one ultrasound image may comprise one or more of a contrast enhanced ultrasound image, a B-mode ultrasound image, or a Doppler ultrasound image. The at least one ultrasound image may comprise a B-mode ultrasound image and a Doppler ultrasound image overlaid over one another. Common anatomical markers in the two images may be identified and mapped to one another to generate the overlaid image. In some cases, a contrast agent may be introduced into the target tissue prior to the ablation to provide more enhanced ultrasound images.

The target tissue may be ablated with one or more of RF energy, thermal energy, cryo energy, ultrasound energy, HIFU energy, optical energy, laser energy, X-ray energy, or microwave energy. The target tissue may be ablated by extending at least one ablation element into the target tissue. The at least one ablation element may comprise one or more of at least one needle or at least one tine. The target tissue may comprise a fibroid, a uterine fibroid, a fibroid tissue, a tumor, a tissue hyperplasia, or an undesired scar tissue.

Aspects of the present disclosure also provide systems for treating a target tissue. A treatment system may comprise a treatment probe, a real-time display, and a controller. The treatment probe may comprise a handle, a probe body, an imaging source coupled to the probe body, and an ablation element coupled to the probe body and configured to ablate the target tissue. The real-time display may be coupled to the treatment probe. The controller may be coupled to the imaging source of the treatment probe and the real-time display. The controller may comprise a computer readable, non-transient storage medium comprising (i) instructions for the imaging source to generate a real-time image of the target tissue during ablation of the target tissue and (ii) instructions for the real-time display to display the real-time image, the real-time image showing blood perfusion of the target tissue, thereby indicating to a user a progress of the ablation.

The ablation element may comprise a needle structure extendable from the treatment probe into the target tissue. The ablation element may further comprise a plurality of needles extendable from the needle structure into the target tissue. The computer readable, non-transient storage medium may further comprise instructions for the real-time display to display a representation of a position of one or more of the needle structure or the plurality of tines on the real-time image.

The computer readable, non-transient storage medium may further comprise instructions for determining a real-time blood perfusion level of the target tissue and determining whether the real-time blood perfusion level is below a threshold amount. The computer readable, non-transient storage medium may further comprise instructions for determining an initial blood perfusion level of the target tissue. The threshold amount may be 50% or less, 45% or less, 40% or less, 35% or less, 30% or less, 25% or less, 20% or less, 15% or less, 10% or less, or 5% or less of the initial blood perfusion amount of the target tissue. The computer readable, non-transient storage medium may further comprise instructions for indicating to the user to halt the ablating of the target tissue in response to the real-time blood perfusion level being below the threshold amount. The initial blood perfusion level may comprise an initial Doppler ultrasound signal within the target tissue. The real-time blood perfusion amount may comprise a real-time Doppler ultrasound signal within the target tissue.

A position of an imaging source in relation to the target tissue may be fixed. The real-time image of the target tissue may be generated during the ablating with the position of the imaging source fixed in relation to the target tissue. The target tissue may be ablated with an ablation element. The imaging source may be fixedly coupled to the ablation element. Alternatively or in combination, the imaging source may be removably coupled to the ablation element.

The real-time image of the target tissue may comprise at least one ultrasound image of the target tissue. The at least one ultrasound image may comprise one or more of a contrast enhanced ultrasound image, a B-mode ultrasound image, or a Doppler ultrasound image. The at least one ultrasound image may comprise a B-mode ultrasound image and a Doppler ultrasound image overlaid over one another. Common anatomical markers in the two images may be identified and mapped to one another to generate the overlaid image. In some cases, a contrast agent may be introduced into the target tissue prior to the ablation to provide more enhanced ultrasound images.

The target tissue may be ablated with one or more of RF energy, thermal energy, cryo energy, ultrasound energy, HIFU energy, optical energy, laser energy, X-ray energy, or microwave energy. The target tissue may be ablated by extending at least one ablation element into the target tissue. The at least one ablation element may comprise one or more of at least one needle or at least one tine. The target tissue may comprise a fibroid, a uterine fibroid, a fibroid tissue, a tumor, a tissue hyperplasia, or an undesired scar tissue.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A illustrates a distal end of the needle component being connected to a distal end of the imaging component.

DETAILED DESCRIPTION OF THE INVENTION

Figure 1:
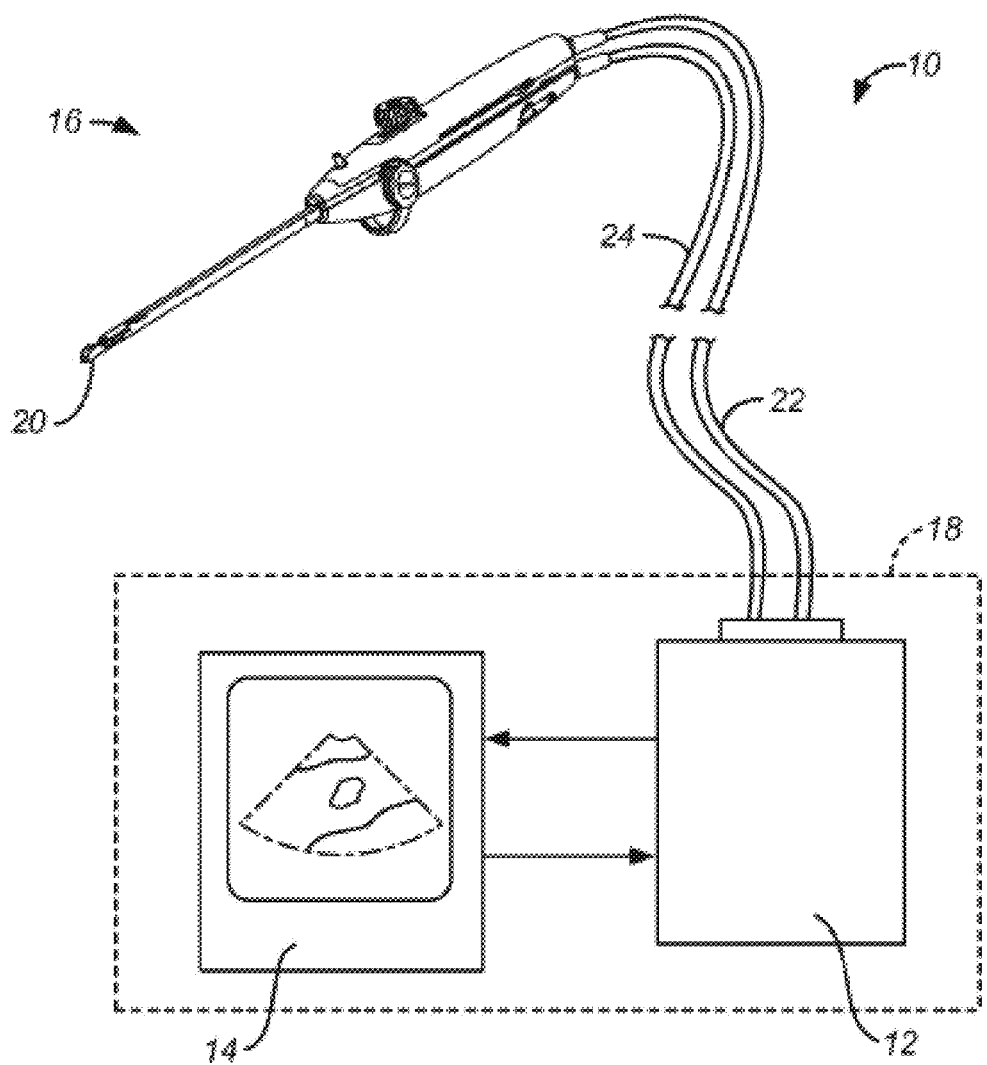
FIG. 1 is a schematic illustration of the system of the present disclosure comprising a system controller, an image display, and a treatment probe having a deployable needle structure and imaging transducer.

As illustrated in FIG. 1, a system 10 constructed in accordance with the principles of the present invention may include a system controller 12, an imaging display 14, and a treatment probe 16. The system controller 12 will typically be a microprocessor-based controller which allows both treatment parameters and imaging parameters to be set in a conventional manner. The display 14 will usually be included in a common enclosure 18 together with the controller 12 but could be provided in a separate enclosure. The treatment probe 16 may include an imaging transducer 20 which may be connected to the controller 12 by an imaging cord 24. The controller 12 may supply power to the treatment probe 16 via a treatment cord 22. The treatment probe 16 may also be in communication with the controller 12 via the treatment cord 22 such as to provide one or more of a control signal, a feedback signal, a position signal, or a status signal, to name a few. The controller 12 will typically further include an interface for the treating physician to input information to the controller 12, such as a keyboard, touch screen, control panel, mouse, joystick, directional pad (i.e., a D-pad), or the like. Optionally, a touch panel may be part of the imaging display 14. The energy delivered to the treatment probe 16 by the controller 12 may be radiofrequency (RF) energy, microwave energy, a treatment plasma, heat, cold (cryogenic therapy), or any other conventional energy-mediated treatment modality. Alternatively or additionally, the treatment probe 16 could be adapted to deliver drugs or other therapeutic agents to the tissue anatomy to be treated. In some embodiments, probe 16 plugs into an ultrasound system and into a separate radio frequency (RF) generator. An interface line connects the ultrasound system and the RF generator.

Figure 2:
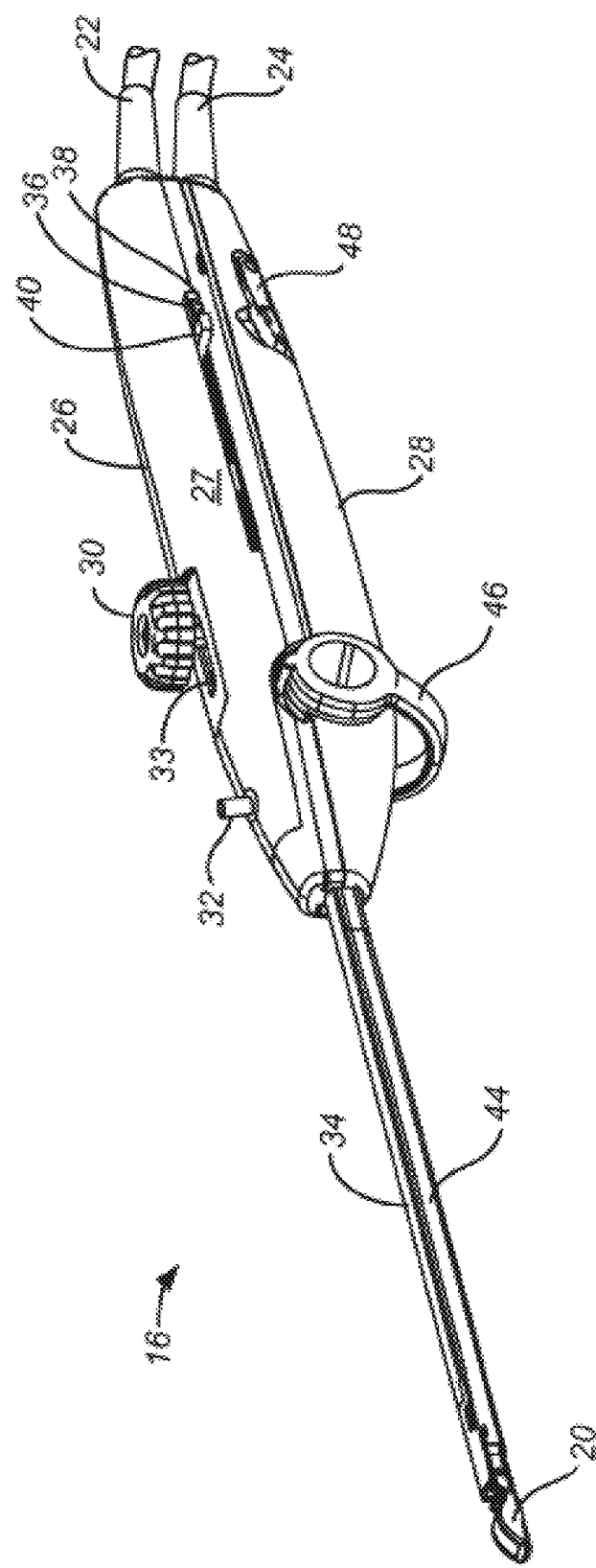
FIG. 2 is a perspective view of the treatment probe of the present disclosure.
Figure 3:
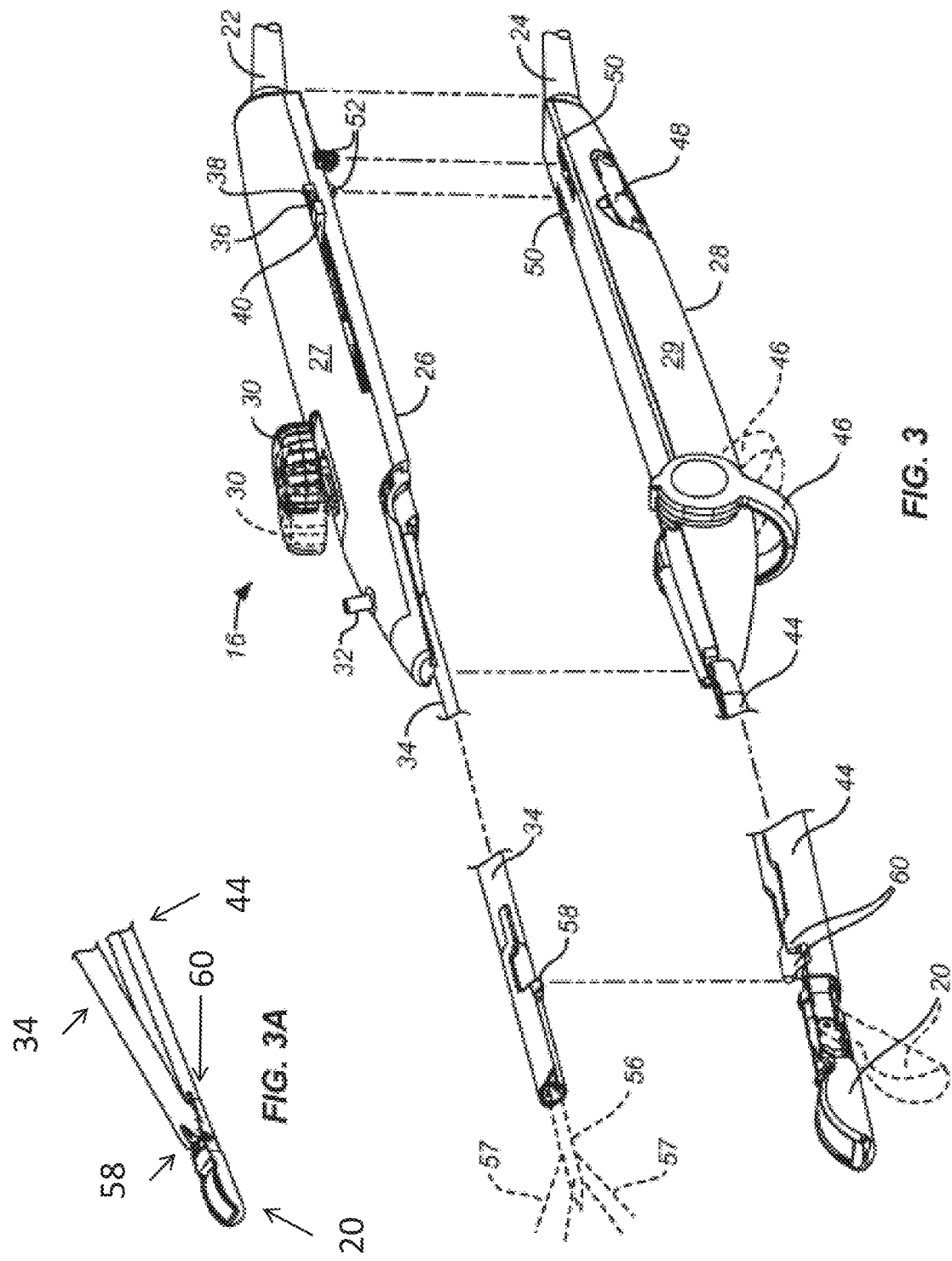
FIG. 3 is a view of the treatment probe of FIG. 2 illustrating an imaging component of the probe separated from a needle component with portions broken away and portions enlarged.

Referring now to FIGS. 2 and 3, the treatment probe 16 may comprise a needle component 26 and an imaging component 28. The needle component 26 and the imaging component 28 may be constructed as separate units or assemblies which may be removably attached to each other for use. After use, the needle component 26 may be separated and will typically be discarded while the imaging component 28 may be sterilized for reuse. The treatment probe 16 is shown in its fully assembled configuration in FIG. 2 and is shown in its disassembled configuration in FIG. 3. In other embodiments of the present invention, the needle component 26 and the imaging component 28 could be combined in a single, integrated handle unit.

The needle component 26 may comprises a handle portion 27 having a control element 30 on its upper surface. The control element 30 may comprise a joystick, a directional pad (i.e., D-pad) or another user interface. The control element 30 may be in communication with the controller 12 to adjust the display 14, adjust treatment parameters, adjust the size and/or position of the targeting region and/or the safety region which are shown on the display 14, and/or perform other functions as will be described in more detail below.

The needle 56 may be deployed from the needle shaft 34, and the needle 56 and optional tines 57 together may form a needle structure which may be constructed, for example, as previously described in commonly owned U.S. Pat. Nos. 8,992,427, 8,206,300, and 8,262,574, the full disclosures of which are incorporated herein by reference.

The handle portion 27 of the needle component 26 may further include a fluid injection port 32 which allows saline or other fluids to be injected through the needle shaft 34 into a target region in the tissue being treated, such as the uterus. The needle handle 27 may also include a needle slide 36, a needle release 38, and a tine slide 40 which are used to deploy the needle 56 and tines 57. The needle slide 36 may be slid forward to advance the needle 56 and may be slid backward to retract the needle 56. The tine slide 40 may be slid forward to advance the tines 57 and may be slid backward to retract the tines 57. In some embodiments, the needle 56 and the tines 57 may be coupled to one or more servos within the body of the handle portion 27 which are configured to actuate the needle 57 and the tines 57, and the needle 56 and the tines 57 may be actuated by operating the control element 30 and/or the controller 12. In many embodiments, the needle 56 must be deployed first before the tines 57 can be deployed. The imaging cord 24 may be attachable at a proximal end of the handle portion 27 of the imaging component 28 for connection to the controller 12, as previously described.

The imaging component 28 may comprise a handle portion 29 and an imaging shaft 44. A deflection lever 46 on the handle portion 29 can be retracted in order to downwardly deflect the imaging transducer 20, as shown in broken line in FIG. 3. A needle component release lever 48 may be coupled to a pair of latches 50 which engage hooks 52 on a bottom surface of the handle portion 27 of the needle component 26. The needle component 26 may be releasably attached to the imaging component 28 by first capturing a pair of wings 58 (only one of which is shown in FIG. 3) on the needle shaft 34 beneath hooks 60 on the imaging shaft 44, as shown in FIG. 3A. A bottom surface of the needle handle portion 27 may then be brought down over an upper surface of the imaging handle portion 29 so that the hooks 52 engage the latches 50 to form a complete assembly of the treatment probe 16, where the handle portions together form a complete handle, for use in a procedure. After use, the needle component release lever 48 may be pulled in order to release the hooks 52 from the latches 50, allowing the handle portions 27 and 29 to be separated.

In use, as will be described in more detail below, the control element 30 may be used to both position (translate) and adjust the size of a virtual treatment region which is projected onto the display 14 of the system 10. The control element 30 may be pressed forward (distally) and pressed backward (proximally) in order to translate the position of the treatment/safety region on the image, for example. The control element 30 may be pressed to the left and/or right to adjust the size of the boundary of the treatment/safety region. For example, the control element 30 may be pressed to the left to shrink the boundary while the control element 30 may be pressed to the right to enlarge the boundary. Once the virtual boundaries of the treatment/safety region have been set on the real-time image, the needle and tines may be automatically advanced to the corresponding deployment positions by moving the needle slide 36 and tine slide 40 until their movement is arrested by the user, for example, as recommended by the stops. The position of the treatment/safety region may also be dependent on the location at which the physician holds the treatment probe 16 within the target tissue. Thus, advancement of the needle 56 and tines 57 using the slides 36 and 40 will result in the proper placement of the needle and tines within the target tissue only if the treatment probe position is held steady from the time the boundaries are set until advancement of the needle/tines is completed. In preferred embodiments, the control element 30 may also be manipulated to adjust the length of and/or power delivery during a treatment protocol. For example, the control element 30 may be pressed to select a different control menu from one for the adjustment of the boundaries, and one of the selectable menus may allow the power delivery parameters to be adjusted such as by pressing up/down to adjust the time length for power delivery and pressing left/right to adjust the amount of power delivered. Another menu may comprise a menu for deploying the needle 56 and the tines 57 by operating the control element 30, such as in embodiments where the needle 56 and the tines 57 are articulated using one or more servos within the handle component 27 of the needle component 26. Yet another menu may be selected to allow the control element 30 to move a cursor on the display 14. Thus, the control element 30 may be used to virtually size the treatment/safety region based not only on the degree to which the tines have been advanced, but also the amount of energy which is being delivered to the target tissue.

Figure 4:
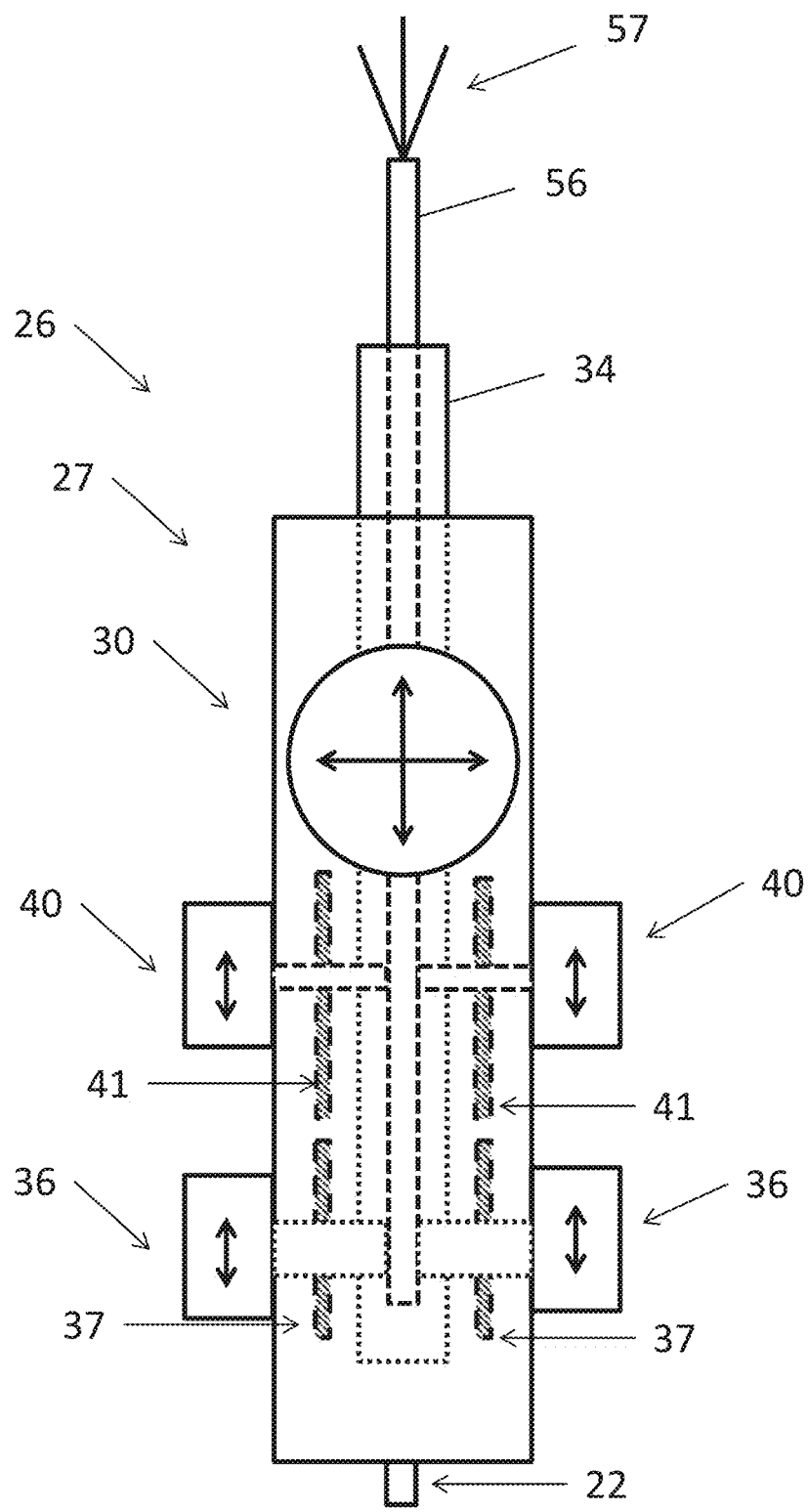
FIG. 4 illustrates a schematic view of the treatment probe of the present disclosure.

FIG. 4 shows a schematic illustration of the needle component 26 of the treatment probe 16. As shown in FIG. 4, the needle component 26 may comprise one or more needle position sensors 37 and one or more tines position sensors 41. The needle position sensor(s) 37 may be coupled to a handle end portion of the needle deployment shaft 34. Advancement and retraction of the needle 56 by the slide 36 can thereby be tracked by the needle position sensor(s) 37. The needle position sensor(s) 37 may generate a position signal for the needle deployment shaft 34 which may be sent to the controller 12 through the treatment cord 22 and from which the position of the needle 56 can be determined. Likewise, the tines position sensor(s) 41 may be coupled to a handle end portion of the tine deployment shaft disposed within the needle deployment shaft 34. Advancement and retraction of the tines 57 by the slide 40 can thereby be tracked by the needle position sensor(s) 37. The tines position sensor(s) 41 may generate a position signal for the tines deployment shaft which may be sent to the controller 12 through the treatment cord 22 and from which the position of the tines 56 can be determined. The needle position sensor(s) 37 and the tines position sensor(s) 41 may comprise any type of position sensor such as a linear encoder, a linear potentiometer, a magnetic sensor, a linear variable differential transformer (LVDT) sensor, a rheostat sensor, or a pulse encoder, to name a few. The positions of the needle 56 and/or tines 57 may be tracked in real time by the position sensors 37, 41 and the controller 12. The calculated treatment and/or safety boundaries may be displayed and adjusted on the display unit 14 as the position of the needle 56 and tines 57 are tracked and optionally updated if moved. Alternatively or in combination, the needle 56 and tines 57 may be translated using one or more servo motors which may additionally provide position information for the needle 56 and the tines 57.

The physician may adjust the control element 30 to locate the boundaries of the treatment/safety region as desired to be shown on the visual display 14.

A particular advantage of this method and system is that the physician can manipulate the treatment/safety boundaries over the target anatomy by either moving the boundaries relative to (or within) the real-time image by manipulating (pressing forward/backward, left/right) the control element 30 or moving the entire real-time image with respect to the target anatomy by manipulating the entire treatment probe 16 in order to get the treatment boundary over the tumor and keeping the safety boundary away from sensitive anatomy. So, before the physician advances any needles into the patient tissue, they can confirm in advance using the virtual targeting interface that the ablation will be effective and safe.

Figure 5:
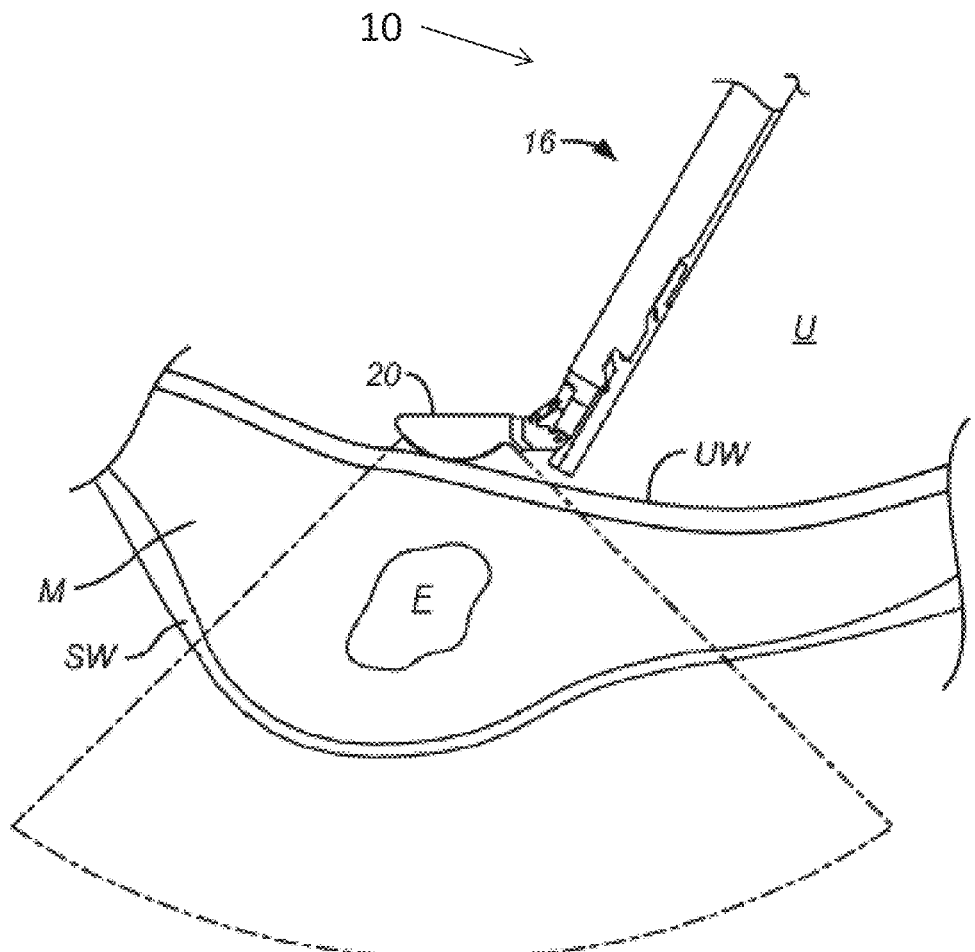
FIG. 5 illustrates a distal portion of the treatment probe introduced into a uterine cavity to image a fibroid in the myometrium.

Referring now to FIG. 5, the system 10 of the present invention can be used to treat a fibroid F located in the myometrium M in a uterus U beneath a uterine wall UW (the endometrium) and surrounded by the serosal wall SW. The treatment probe 16 can be introduced transvaginally and transcervically (or alternately laparoscopically) to the uterus, and the imaging transducer 20 deployed to image the fibroid within a field of view indicated by the broken lines.

Figure 6A:
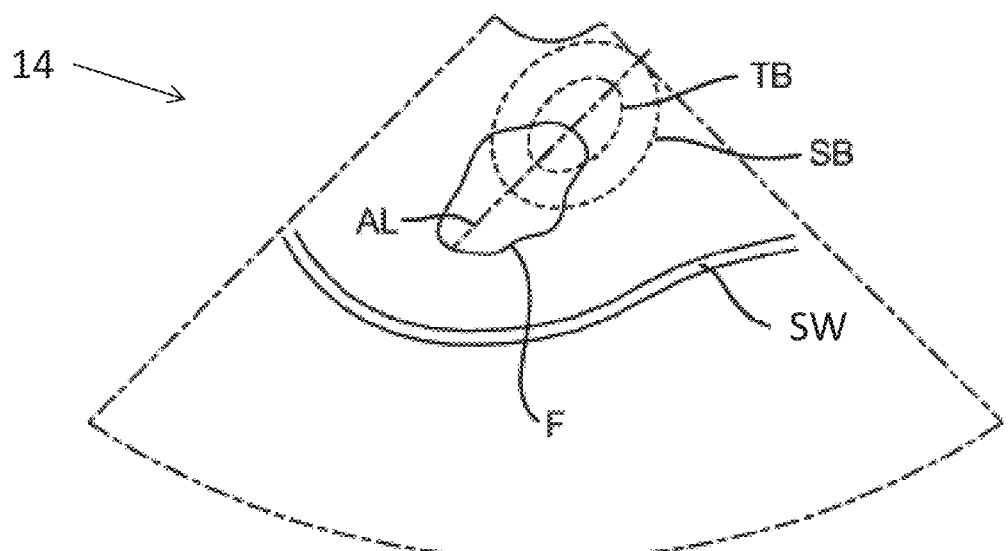
FIGS. 6A, 7A, 8A, 9A, 10A, and 11A illustrate "screenshots" of the real-time image display as treatment and safety boundaries are being adjusted and the ablation elements of the treatment probe are advanced into target tissue, in accordance with the principles of the present disclosure.
Figure 6B:
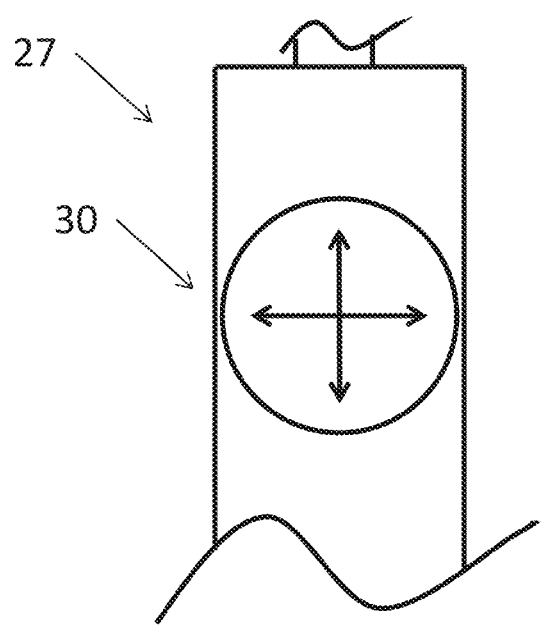
FIGS. 6B, 7B, 8B, 9B, 10B, and 11B illustrate manipulation of the handle which corresponds to the repositioning of the projected images of the treatment and safety boundaries on the real-time images of FIGS. 6A, 7A, 8A, 9A, 10A, and 11A, respectively.
Figure 7A:
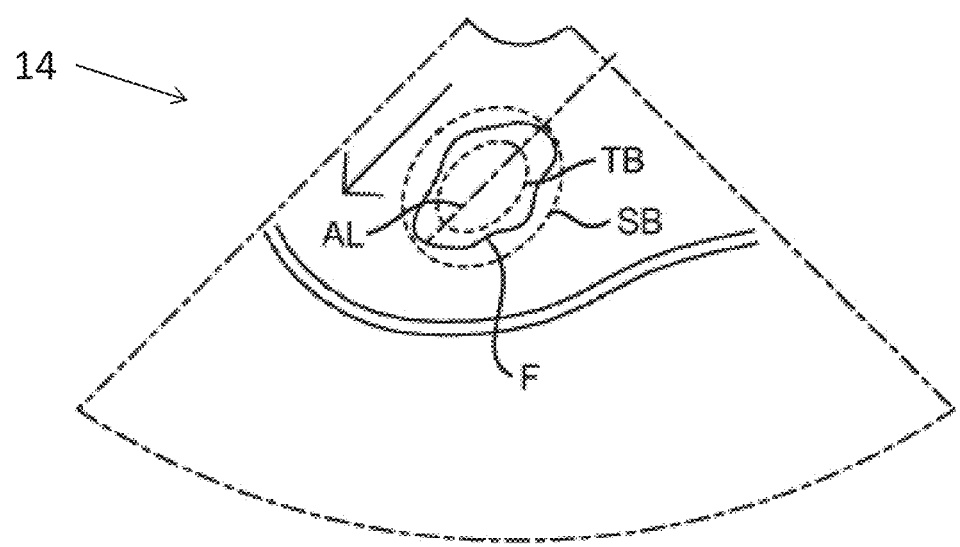
Figure 7B:
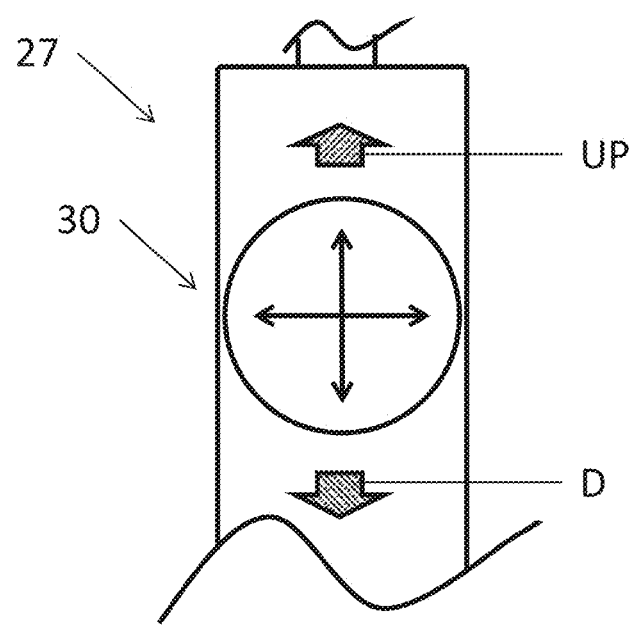

Once the fibroid is located on the display 14, as shown in FIG. 6A, the control element 30 on the handle component 27 can be used to locate and size both a treatment boundary TB and a safety boundary SB. Initially, as shown in FIG. 6A, the virtual boundary lines TB and SB may neither be positioned over the fibroid nor properly sized to treat the fibroid, and the control element 30 may be in a neutral position as shown in FIG. 6B. Prior to actual needle and tine deployment, the physician may want to both position and size the boundaries TB and SB for proper treatment. As the imaging transducer 20 may already be positioned against the uterine wall UW, the only way to advance the treatment and safety boundaries TB and SB is to move the boundaries forward by manipulating the control element 30, such as by pressing the control element 30 forward in the direction of arrow UP as shown in FIG. 7B. This manipulation may cause the treatment and safety boundaries TB and SB to move forwardly along the axis line AL. This manipulation may also cause the virtual boundaries on the real-time image display 14 to move over the image of the fibroid, as shown in FIG. 7A. If the treatment and safety boundaries TB and SB need to be retracted, the control element 30 may be manipulated such as by pressing the control element 30 backward in the direction of arrow D as shown in FIG. 7B.

Figure 8A:
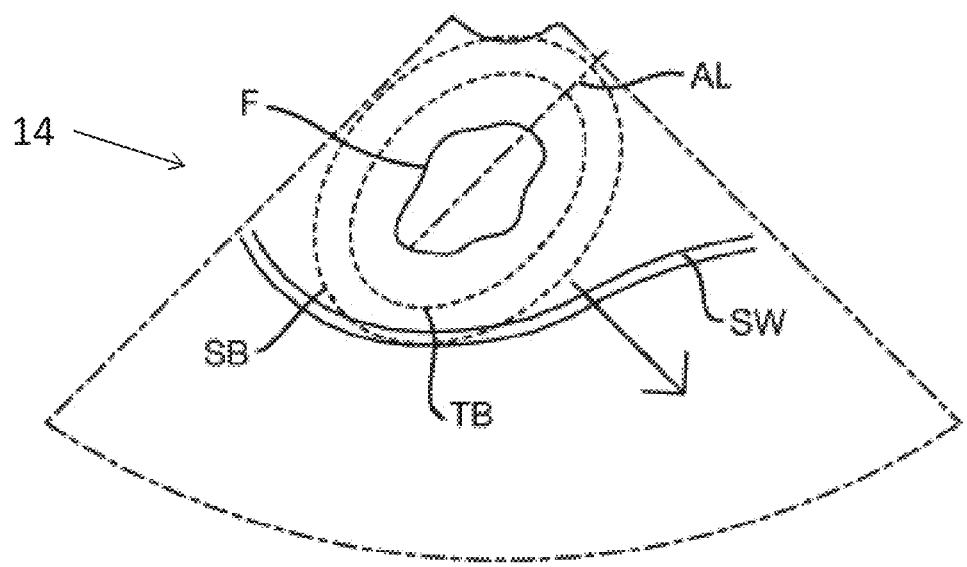
Figure 8B:
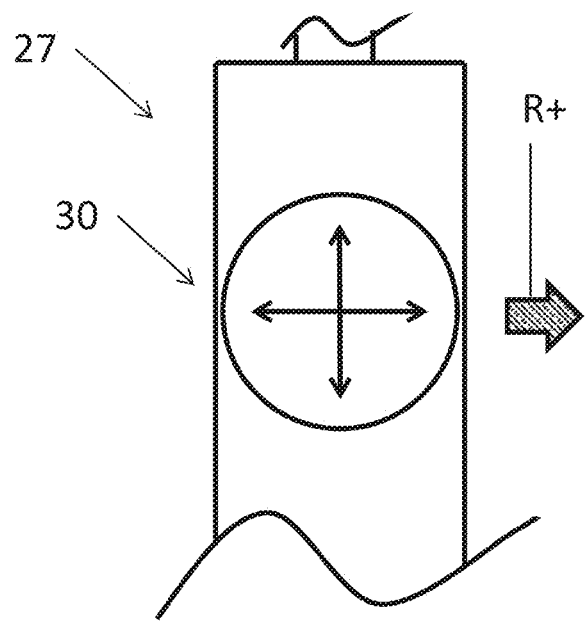
Figure 9A:
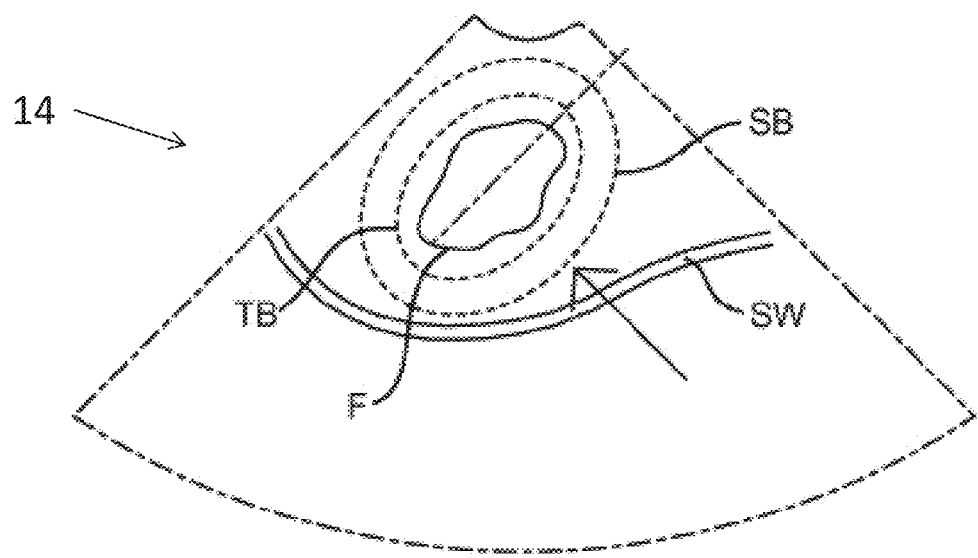
Figure 9B:
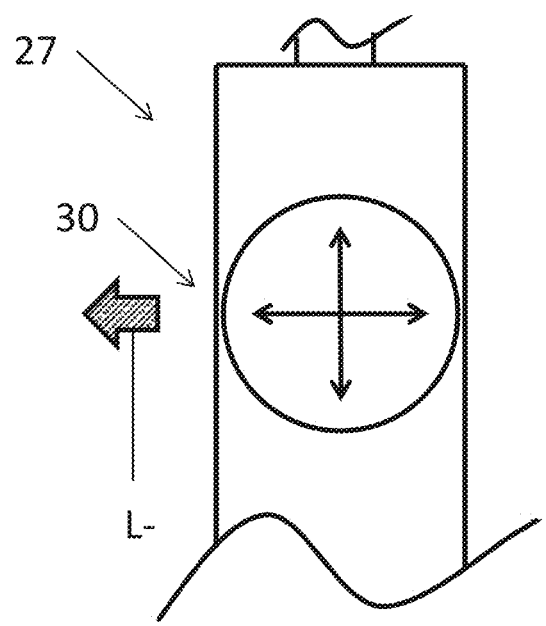

As shown in FIG. 7A, however, the size of the treatment boundary TB may be insufficient to treat the fibroid since the boundary does not extend over the image of the fibroid. Thus, it may be necessary to enlarge the treatment boundary TB by manipulating the control element 30, as shown in FIG. 8B, such as by pressing the control element 30 to the right in the direction of arrow R+. This may enlarge both the treatment boundary TB and the safety boundary SB, as shown in FIG. 8A. While the enlarged virtual treatment boundary TB may now be sufficient to treat the fibroid, the safety boundary SB has extended over the serosal wall SW, as also shown in FIG. 8A. Thus, there may be a risk that the treatment would affect more sensitive tissue surrounding the uterus, and it may be necessary that the virtual safety boundary SB be retracted by again manipulating the control element 30 in an opposite direction, such as by pressing the control element 30 to the left in the direction of arrow L− as shown in FIG. 9B. This manipulation may reduce the size of both the safety and treatment boundaries SB and TB, as shown in FIG. 9A, and the physician may have confirmation that the treatment may be effective because the treatment boundary TB completely surrounds the fibroid on the real-time image display, and that the treatment will be safe because the safety boundary SB is located within the myometrium M and does not cross the serosal wall SW on the real-time image display.

Figure 10A:
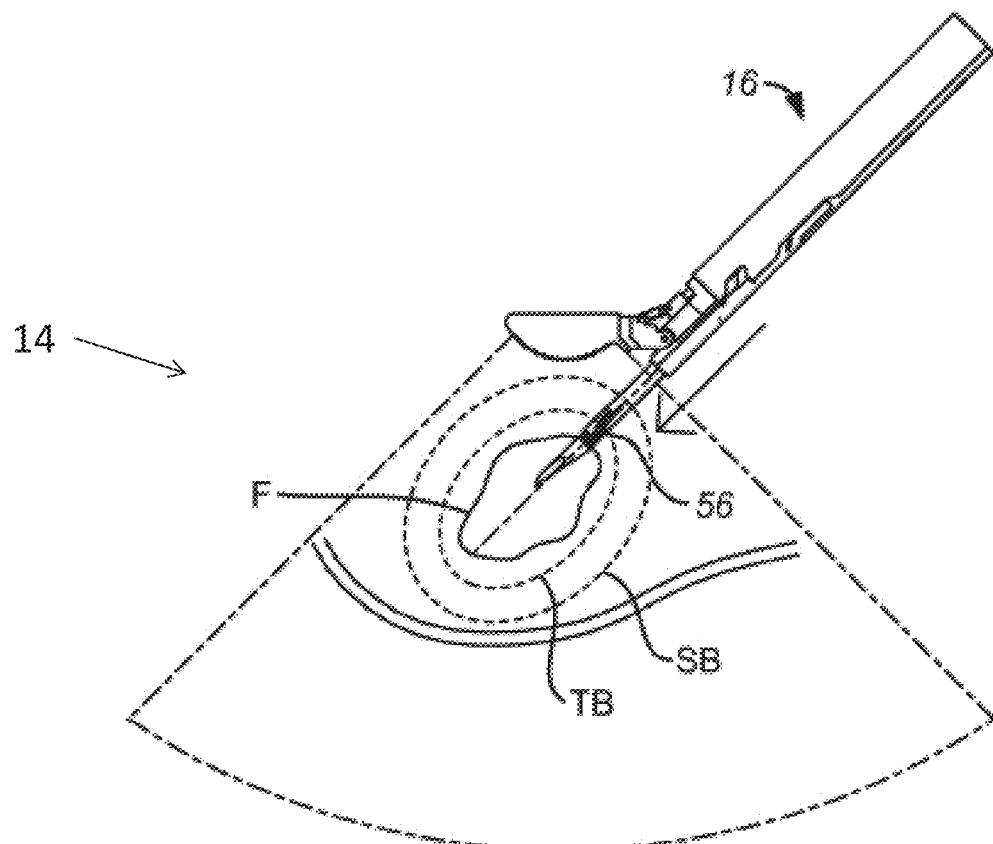
Figure 10B:
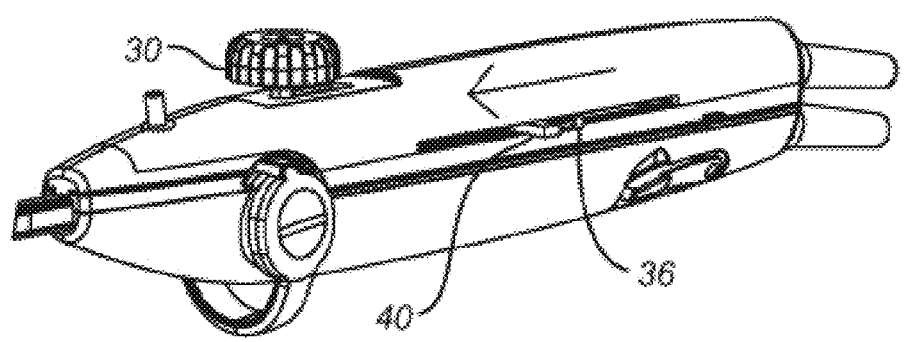

While holding the treatment probe 16 steady, the physician may then advance the needle slide 36, as shown in FIG. 10B, causing the needle 56 to extend into the fibroid F, as shown in FIG. 10A. The illustration in FIG. 10A includes a representation of the treatment probe 16 which may correspond to the physical probe which is present in the patient. The remainder of FIG. 10A corresponds to the image present on the target display 14. The treatment and safety boundaries TB, SB may determine a virtual stop indicator or fiducial 142 for the needle 56. The target display 14 may include a position indicator 140 for the needle 56, in many cases the tip of the needle 56. In some cases, the positions of the virtual stop indicators or fiducials may correlate with the size and position of the treatment and safety boundaries TB and SB. In other cases, the positions of the virtual stop indicators or fiducials may be adjusted independently with respect to the treatment and safety boundaries TB and SB.

Figure 11A:
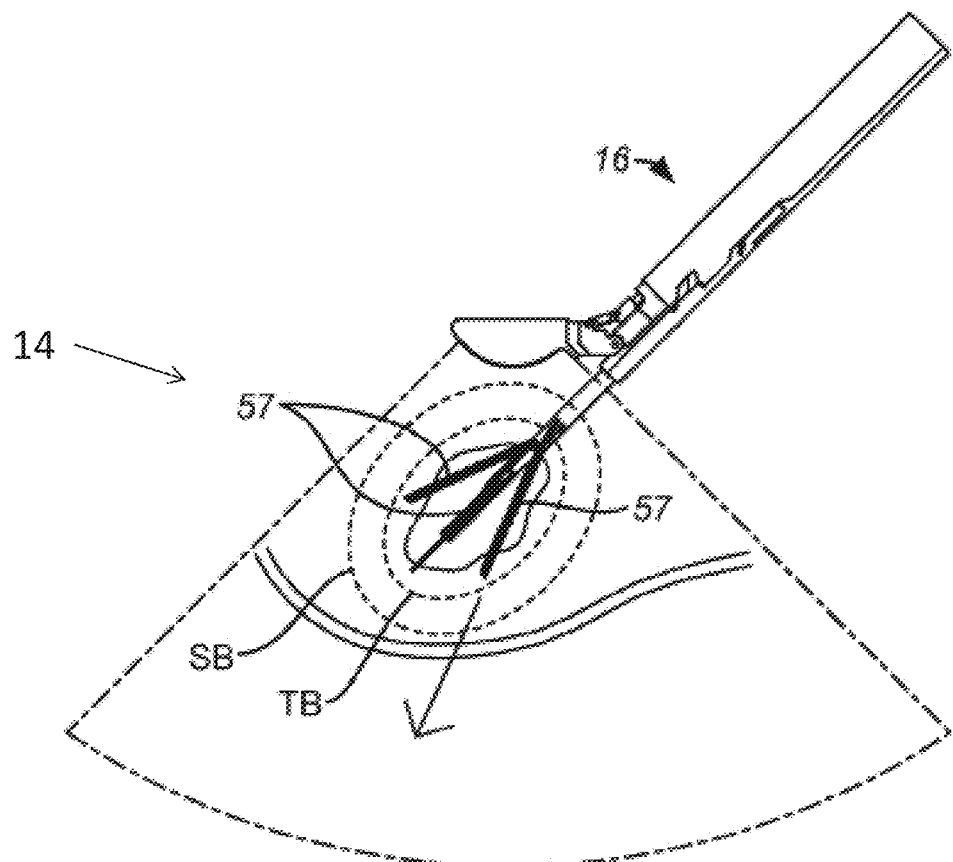
Figure 11B:
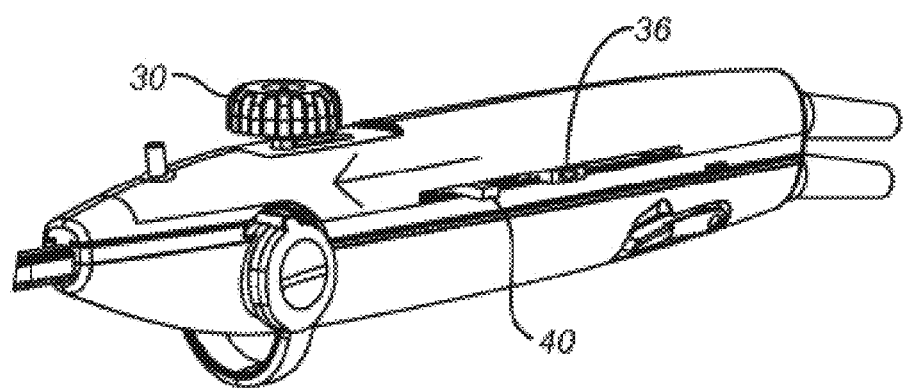

After the needle 56 has been fully deployed as indicated by the overlap of the needle position indicator 140 and the stop fiducial 142, the tines 57 may be deployed by advancing the tine slide 40, as shown in FIG. 11B. Optionally, the treatment probe 16 may be rotated about a central axis (typically aligned with the axis of the needle 56) to confirm the treatment and safety boundaries TB, SB in all planes of view about the fibroid. The needle 56 and the tines 57 may remain in place relative to the fibroid F while the remainder of the treatment probe 16 is rotated about the fibroid F. Display 14 may show the position of the treatment and safety boundaries TB and SB in real time relative to the target fibroid F and serosal wall SW. The tines may be configured as shown in FIG. 11A, and power can be supplied to the tines 57 (and optionally the needle 56) in order to achieve treatment within the boundary depicted by the virtual treatment boundary TB. Again, FIG. 11A may mix both the virtual image which would be present on the display 14 as well as the physical presence of the treatment probe 16.

With the needle 56 and the tines 57 in the desired position, the treatment probe 16 may be operated to begin ablation of the target fibroid F. The position of the imaging transducer 20 relative to the target fibroid F may be fixed throughout the ablation. Because of the fixed relative position of the imaging transducer 20, for example, real-time images of the treatment space, including the target fibroid F and the serosal wall SW, can be accurately compared at different time points across the ablation process.

Figure 12:
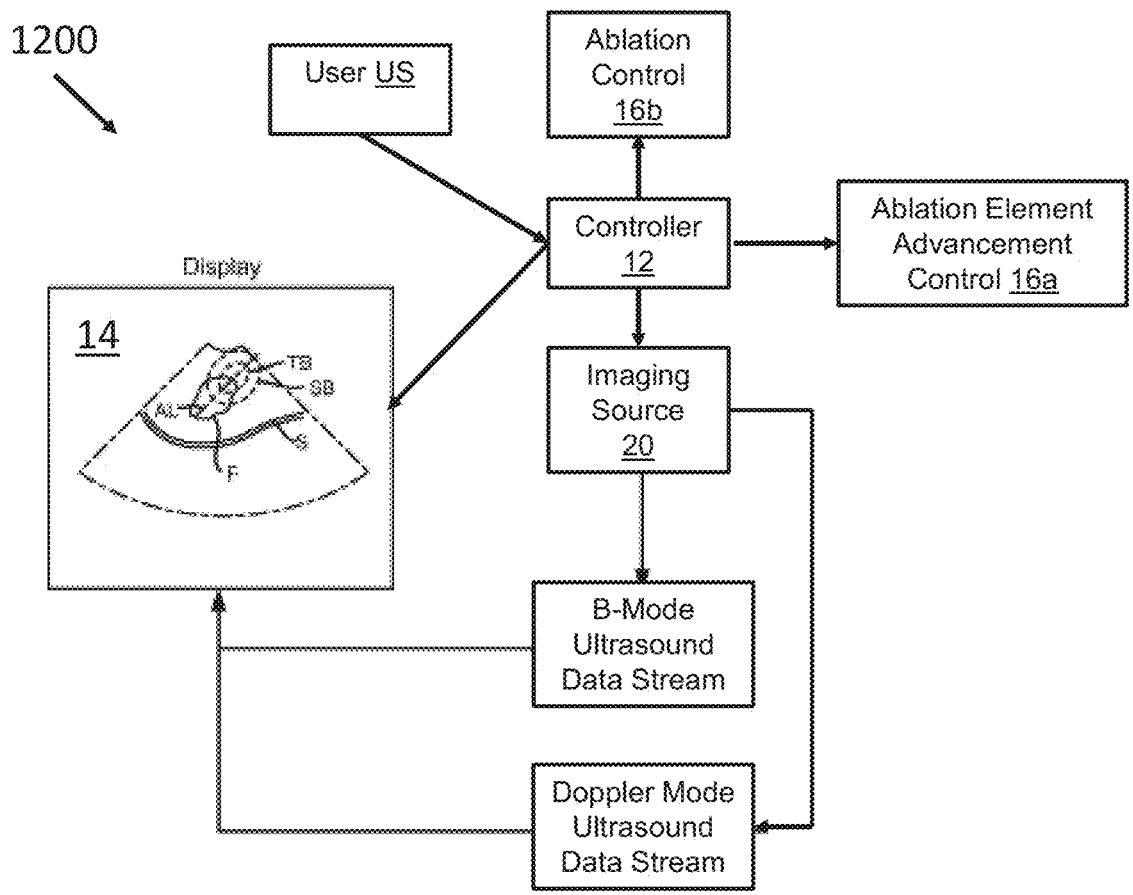
FIG. 12 illustrates a system diagram where a B-mode ultrasound data stream (showing tissue morphology) is combined with a Doppler mode ultrasound data stream to generate a real-time image, according to the present disclosure.

FIG. 12 shows a diagram of the tissue treatment system 1200. The user US may operate the controller 12, which as discussed above may be coupled to the treatment probe 16 to advance or retract the needle structure 56 and the plurality of tines 57, i.e., the ablation element, as shown by the ablation element advancement control 16a. The user US may also operate the controller 12, through the treatment probe 16 in many cases, to start or stop ablation with the needle structure 56 and the plurality of tines 57, as shown with the ablation control 16b. As further shown by FIG. 12, the controller 12 may also operate the imaging source 20 to acquire one or more ultrasound images. In many embodiments, the imaging source 20 acquires both one or more B-mode ultrasound images and one or more Doppler mode ultrasound image, which the controller 12 may direct the system display 14 to show as a combined image showing both tissue morphology and blood perfusion. The imaging source 20 may be directed to acquire B-mode ultrasound images and Doppler mode ultrasound images at intervals. For example, ultrasound images may be acquired at a rate of 1 to 100 frames per second, with the frames alternating between B-mode and Doppler mode.

Figure 13:
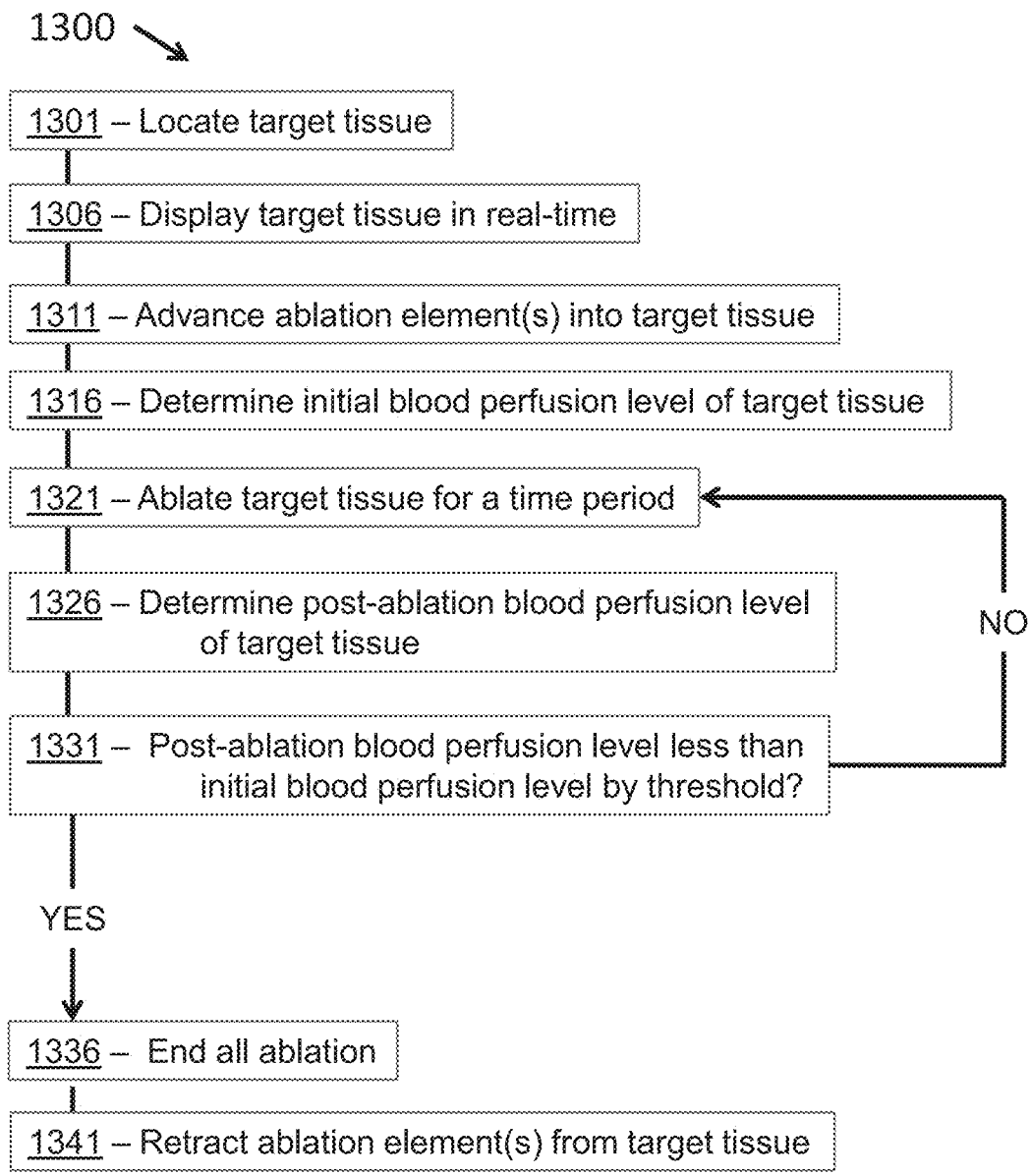
FIG. 13 illustrates a flow chart of a method of treating tissue, according to the present disclosure.

FIG. 13 shows a method 1300 for treating a tissue according to the present disclosure. The systems and devices described herein may be used to implement the method 1300, including any combination of the steps and sub-steps thereof In a step 1301, a target tissue structure, such as target fibroid F, may be located.

In a step 1306, a real-time display of the target tissue structure may be displayed as described herein. In some embodiments, a contrast agent may be introduced to the target tissue to enhance the image of the structural and morphological features of the target tissue such that they may be better tracked during the ablation. In some embodiments, the features of the Doppler ultrasound image indicating blood perfusion may be enhanced as well. Contrast agents that may be appropriate may include some commercially available contrast agents such as Optison®, Definity®, Echovist®, Sonazoid® and SonoVue®, to name a few.

In a step 1311, one or more ablation elements, such as the needle structure 56 and the plurality of tines 57, may be advanced into the target tissue.

In a step 1316, the initial blood perfusion level of the target tissue may be determined, such as by observing and/or quantifying a Doppler ultrasound image which may be taken by the imaging source 20.

In a step 1321, the target tissue may be ablated for a predetermined time period, for example, 0.5 to 20 minutes for a single ablation.

In a step 1326, the blood perfusion level of the target tissue may be determined after the predetermined treatment time period. For example, the user may manually make this determination by viewing the updated real-time image including Doppler ultrasound and/or contrast enhanced ultrasound information. Alternatively or in combination, the controller 12 may include be configured to quantify the current level of blood perfusion and direct the display 14 to show the quantified amount of blood perfusion.

In a step 1331, this current "post-ablation" blood perfusion level may be compared to the initial blood perfusion level. If the current blood perfusion level is not below a threshold as compared to the initial blood perfusion level, the step 1321 of ablating the target tissue and so forth may be repeated. If the current blood perfusion level is below the threshold, the protocol may proceed to a step 1336 whereby the ablation of the target tissue is ended. The threshold may comprise, for example, 50% or less, 45% or less, 40% or less, 35% or less, 30% or less, 25% or less, 20% or less, 15% or less, 10% or less, or 5% or less of the initial blood perfusion amount of the target tissue. In some embodiments, a 30% or more reduction of blood perfusion (i.e., current blood perfusion level being 30% or less of the initial) may be considered a successful treatment.

In some embodiments, the perfusion monitoring of the ablation boundary during the treatment is used as a treatment guidance tool. The ablation may be stopped if the user or system observes that the treatment area has propagated outside the targeted area. A contrast agent enhanced image may also facilitate such user observation. The ablation may be interrupted or halted manually or automatically to ensure patient safety.

Finally, in a step 1341, the ablation elements, typically the needle structure 56 and the tines 57, may be retracted form the target tissue. The treatment probe 16 may then be retracted from the surgical field entirely or may be repositioned to treat another target tissue structure.

Although the above steps show method 1300 of treating tissue in a patient according to many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 1300 may be performed with circuitry within the controller 12, the treatment probe 16, or within another system component. The circuitry may comprise one or more of a processor or logic circuitry such as the programmable array logic or a field programmable gate array. The circuitry may be programmed to provide one or more of the steps of the method 1300, and the program may comprise program instructions stored on a non-transient computer readable memory or programmed steps of the logic circuitry such as the programmable array logic or the field programmable gate array.

FIGS. 14A through 14D show exemplary real-time images of a target fibroid F during the ablation protocol as described herein. As described herein, these real-time images may comprise a B-mode ultrasound image showing tissue morphology overlaid with a Doppler mode ultrasound image showing blood perfusion as taken at various time points.

Figure 14A:
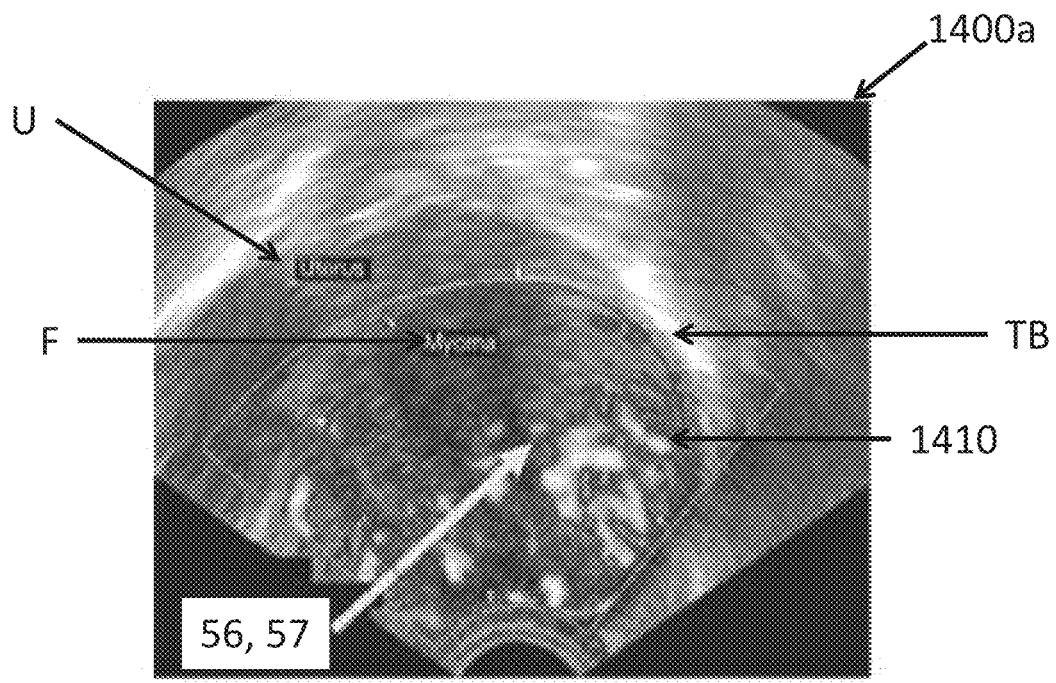
FIGS. 14A, 14B, 14C, and 14D illustrate various real-time images of a target tissue structure as it is ablated, according to the present disclosure.

FIG. 14A shows a first real-time image 1400a showing the uterus U and the target uterine fibroid F. A treatment boundary TB may have been established to surround the target uterine fibroid F. The treatment boundary TB may be centered on the location of the ablation element(s), such as the needle structure 56 and the plurality of tines 57 extending therefrom. The first real-time image 1400a shows the treatment space before any ablation has occurred, and with the Doppler signal(s) 1410 received and shown on the image 1400a defined as a 100% initial Doppler signal. The level of the Doppler signal(s) 1410 within the treatment boundary TB may be determined. In the first real-time image 1400a, for example, 80% of the initial Doppler signals 1410 may be within the treatment boundary TB. As discussed herein, the Doppler signal(s) 1410 indicate areas of high blood perfusion. In some embodiments, the treatment boundary TB may be determined and/or adjusted based on the distribution and/or location of the Doppler signal(s) 1410 showing high blood perfusion. For example, the outer extent of treatment boundary TB may be selected to capture a majority of the high blood perfusion areas, and/or the treatment boundary TB may be centered on a high perfusion area as a focal area of the ablation. The treatment boundary TB and the safety boundary SB may be adjusted with the controller 12 and/or treatment probe 16 as described above.

Figure 14B:
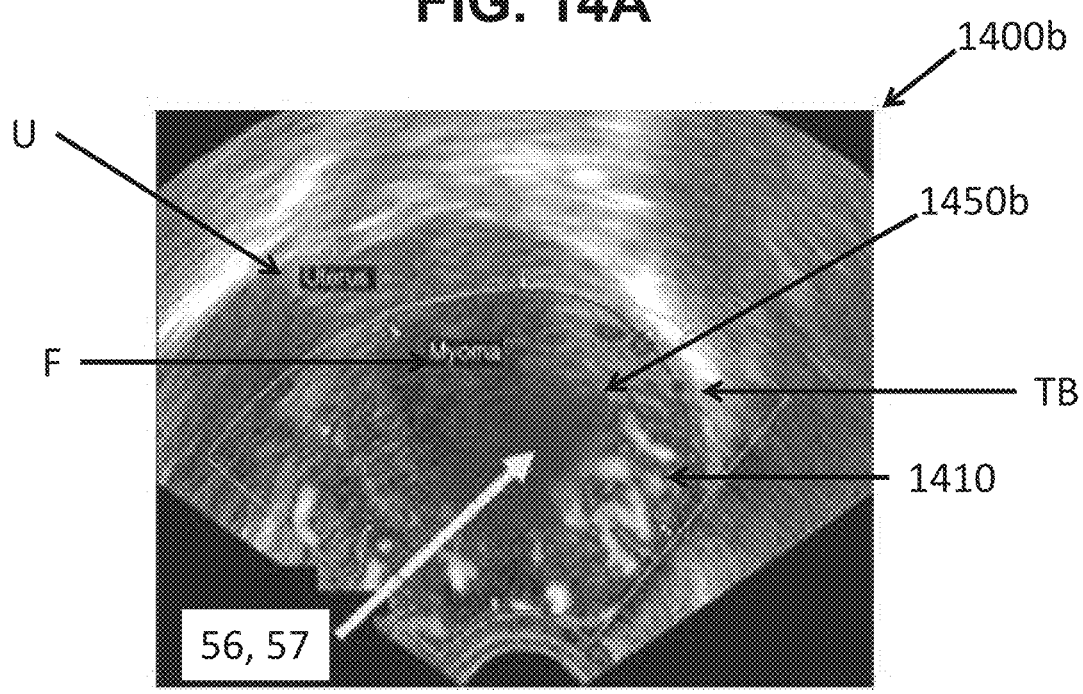

FIG. 14B shows a second real-time image 1400b showing the uterus U and the target uterine fibroid F after a first time period of ablation. As shown in the second real-time image 1400b, an ablated area 1450b may now be present within the treatment boundary TB. The ablated area 1450b may be visible on the B-mode image component of the real-time image 1400b and/or may be visible on the Doppler mode image component of the real-time image 1400b with no Doppler signal within the boundaries of the ablated area 1450b. The level of the Doppler signal(s) 1410 may be reduced after the first predetermined time period of ablation. In the second real-time image 1400b, for example, the total level of the Doppler signals 1410 may be 75% of the initial level shown by FIG. 14A. In some embodiments, the level of the Doppler signal(s) 1410 within the treatment boundary TB may be determined and compared to the initial level to determine a completion percentage of the treatment.

Figure 14C:
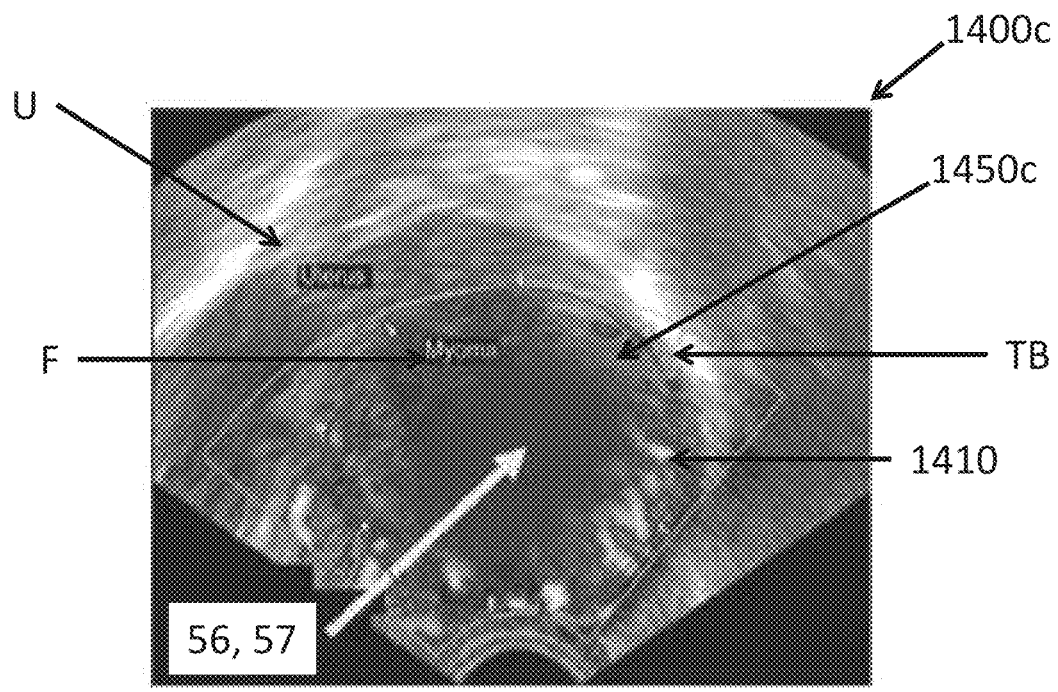

FIG. 14C shows a third real-time image 1400c showing the uterus U and the target uterine fibroid F after a further time period of ablation. As shown in the third real-time image 1400c, the ablated area 1450c within the treatment boundary TB may now be even larger than before, and there may now be 50% of the initial Doppler signal(s) 1410. Again, the level of the Doppler signal(s) 1410 within the treatment boundary TB may be determined and may be used to determine a completion percentage of the treatment.

Figure 14D:
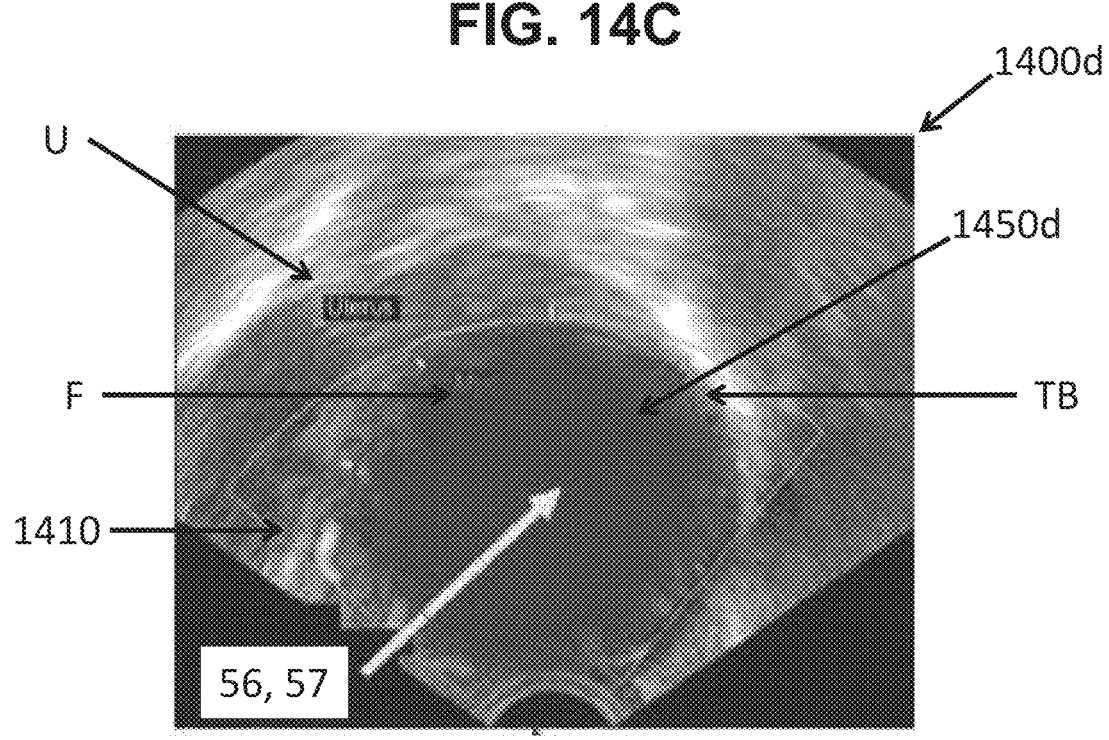

FIG. 14D shows a fourth real-time image 1400d showing the uterus U and the target uterine fibroid F after yet a further time period of ablation. As shown in the fourth real-time image 1400d, the ablated area 1450d within the treatment boundary TB may now nearly match the treatment boundary TB, and there may be very little to no Doppler signal(s) 1410 with the treatment area TB, indicating that the treatment or ablation of the uterine fibroid F is complete. The relative level of the Doppler signal(s) within the treatment boundary may be used as an indicator of ablation or treatment completion. For instance, the ablation or treatment may be indicated as complete if the Doppler signal(s) 1410 currently within the treatment boundary TB has been reduced to 50% or less, 45% or less, 40% or less, 35% or less, 30% or less, 25% or less, 20% or less, 15% or less, 10% or less, or 5% or less of the initial level of Doppler signal(s) 1410, i.e., blood perfusion, within the treatment boundary TB. The exact percentage may be user-selected based on his or her preference. In some embodiments, the controller 12 may allow the user to enter this selection as an ablation parameter to be displayed and tracked. Also, there may still be Doppler signal(s) 1410 outside of the treatment boundary TB. As shown in FIG. 14D, the total level of Doppler signal(s) 1410 within the overall image is 20% of the initial level.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for treating a target tissue, the system comprising:
   a treatment probe comprising a handle, a probe body, an imaging source coupled to the probe body, and an ablation element coupled to the probe body and configured to ablate the target tissue;
   a real-time display coupled to the treatment probe; and
   a controller coupled to the imaging source of the treatment probe and the real-time display, the controller comprising a computer readable, non-transient storage medium comprising:
   (i) instructions for the imaging source to generate a real-time image of the target tissue during ablation of the target tissue,
   (ii) instructions for the real-time display to display the real-time image, the real-time image showing the target tissue and a virtual treatment boundary around the target tissue,
   (iii) instructions for determining an initial blood perfusion of the target tissue,
   (iv) instructions for, prior to initiating ablation of the target tissue, modifying one or more of a size or location of the virtual treatment boundary based on the determined initial blood perfusion of the target tissue, and
   (v) instructions for determining a real-time blood perfusion level within the virtual treatment boundary, and determining a completion percentage of the ablation of the target tissue within the virtual treatment boundary based on the determined real-time blood perfusion level within the virtual treatment boundary, thereby indicating to a user a progress of the ablation of the target tissue.

2. A system as in claim 1, wherein the ablation element comprises a needle structure extendable from the treatment probe into the target tissue.

3. A system as in claim 2, wherein the ablation element further comprises a plurality of needles extendable from the needle structure into the target tissue.

4. A system as in claim 1, wherein the computer readable, non-transient storage medium further comprises instructions for the real-time display to display the real-time blood perfusion level on the real-time image.

5. A system as in claim 1, wherein the computer readable, non-transient storage medium further comprises instructions for determining whether the determined real-time blood perfusion level within the virtual treatment boundary is below a threshold amount, and indicating to the user to halt ablation of the target tissue in response to the real-time blood perfusion level being below the threshold amount.

6. A system as in claim 5, wherein the threshold amount is a percentage threshold amount, and wherein the computer readable, non-transient storage medium further comprises instructions for determining an initial blood perfusion level within the virtual treatment boundary, determining a percentage decrease of the determined real-time blood perfusion level within the virtual treatment boundary relative to the determined initial blood perfusion level within the virtual treatment boundary, and indicating to the user to halt ablation of the target tissue in response to the determined percentage decrease of the determined real-time blood perfusion level within the virtual treatment boundary being below the percentage threshold amount.

7. A system as in claim 6, wherein the percentage threshold amount is 50% or less, 45% or less, 40% or less, 35% or less, 30% or less, 25% or less, 20% or less, 15% or less, 10% or less, or 5% or less of the initial blood perfusion amount of the target tissue.

8. A system as in claim 6 1, wherein determining the initial blood perfusion of the target tissue comprises determining Doppler ultrasound signals in the target tissue, and wherein determining the real-time blood perfusion level within the virtual target boundary comprises determining a level of Doppler ultrasound signals within the virtual target boundary.

9. A system as in claim 1, wherein a position of the imaging source is configured to be fixed in relation to the target tissue during the ablation of the target tissue.

10. A system as in claim 9, wherein the real-time image of the target tissue is generated during the ablation with the position of the imaging source fixed in relation to the target tissue.

11. A system as in claim 1, wherein the imaging source is configured to be in a fixed position in relation to the ablation element.

12. A system as in claim 1, wherein the imaging source is configured to be movable relative to the ablation element.

13. A system as in claim 1, wherein the real-time image of the target tissue comprises at least one ultrasound image of the target tissue.

14. A system as in claim 13, wherein the at least one ultrasound image comprises one or more of a contrast enhanced ultrasound image, a B-mode ultrasound image, or a Doppler ultrasound image.

15. A system as in claim 14, wherein the at least one ultrasound image comprises a B-mode ultrasound image and a Doppler ultrasound image overlaid over one another.

16. A system as in claim 1, wherein the target tissue comprises a fibroid, a uterine fibroid, a fibroid tissue, a tumor, a tissue hyperplasia, or an undesired scar tissue.

17. A system as in claim 1, wherein the computer readable, non- transient storage medium further comprises instructions for the real-time display to superimpose the real-time virtual treatment boundary over the real-time image.

18. A system as in claim 1, wherein the computer readable, non-transient storage medium further comprises instructions for the real-time display to display the determined completion percentage of the ablation of the target tissue within the virtual treatment boundary to the user.

19. A system as in claim 1, wherein the computer readable, non-transient storage medium further comprises instructions for determining a real-time virtual ablation boundary based on a real-time blood perfusion in the target tissue, and alerting the user if the real-time virtual ablation boundary is outside of the virtual treatment boundary.

20. A system as in claim 1, wherein the computer readable, non- transient storage medium further comprises instructions for modifying the one or more of the size or location of the virtual treatment boundary in response to user manipulation of one or more control elements.

* * * * *